United States Patent [19]

Arrowsmith et al.

[11] Patent Number: 5,130,334

[45] Date of Patent: Jul. 14, 1992

[54] INDANE SULFONAMIDE ANTI-ARRHYTHMIC AGENTS

[75] Inventors: John E. Arrowsmith, Deal; Peter E. Cross, Canterbury, both of England

[73] Assignee: Pfizer Inc., New York, N.Y.

[21] Appl. No.: 303,226

[22] Filed: Jan. 30, 1989

Related U.S. Application Data

[63] Continuation of Ser. No. 158,465, Feb. 22, 1988, Pat. No. 4,829,071.

[30] Foreign Application Priority Data

Mar. 25, 1987 [GB] United Kingdom ............... 8707122

[51] Int. Cl.$^5$ .................. C07D 307/87; A61K 31/34
[52] U.S. Cl. ..................... 514/469; 548/469; 514/311; 546/171; 546/28
[58] Field of Search ............. 549/469; 514/469, 311; 546/171

[56] References Cited

U.S. PATENT DOCUMENTS

| | | | |
|---|---|---|---|
| 2,456,911 | 12/1948 | Bruce et al. | 260/287 |
| 3,513,239 | 5/1970 | Willey et al. | 514/469 |
| 3,923,813 | 12/1975 | Vanhoff et al. | 260/293.62 |
| 4,192,888 | 5/1980 | Bondinell et al. | 424/321 |
| 4,432,993 | 2/1984 | Ferris | 514/469 |
| 4,435,422 | 3/1984 | Lee et al. | 514/469 |
| 4,656,190 | 4/1987 | Shen et al. | 514/529 |

FOREIGN PATENT DOCUMENTS

| | | | |
|---|---|---|---|
| 0164895 | 12/1985 | European Pat. Off. | |
| 0286277 | 10/1988 | European Pat. Off. | 546/171 |
| 1024650 | 3/1966 | United Kingdom | 549/469 |

*Primary Examiner*—David B. Springer
*Attorney, Agent, or Firm*—Peter C. Richardson; Paul H. Ginsburg

[57] ABSTRACT

Novel 5-alkanesulphonamido-2-[N-(alkanesulphonamidoheterocyclicmethyl)-N-methylamino]indane compounds have been prepared, including their pharmaceutically acceptable salts and various key novel intermediates therefor. The heterocyclic moiety present in these compounds is a benzofused heteroclyclic group derived from either benzofuran or quinoline, and it is attached to the adjacent methyl group of the molecule by means of the available ring carbon atom which is situated alpha to the hetero atom. These compounds are useful in therapy as anti-arrhythmic agents and therefore, are of value in the treatment of various cardiac arrhythmias. The most preferred member compound is 5-methanesulphonamido-2-[N-(5-methanesulphonamidobenzofur-2-ylmethyl)-N-methylamino]indane. Methods for preparing these compounds from known starting materials are provided.

8 Claims, No Drawings

INDANE SULFONAMIDE ANTI-ARRHYTHMIC AGENTS

This is a continuation of application Ser. No. 07/158,465, filed on Feb. 22, 1988, U.S. Pat. No. 4,829,071.

BACKGROUND OF THE INVENTION

This invention relates to certain indane sulfonamides which are antiarrhythmic agents, and to intermediates therefor.

The antiarrhythmic agents of the invention prolong the duration of the action potential in cardiac muscle and conducting tissue, and thereby increase refractoriness to premature stimuli. Thus, they are Class III antiarrhythmic agents according to the classification of Vaughan Williams (Anti-Arrhythmic Action, E. M. Vaughan Williams, Academic Press, 1980). They are effective in atria, ventricles and conducting tissue both in vitro and in vivo and are therefore useful for the prevention and treatment of a wide variety of ventricular and supraventricular arrhythmias including atrial and ventricular fibrillation. Because they do not alter the speed at which impulses are conducted, they have less propensity than current drugs (mostly Class I) to precipitate or aggravate arrhythmias, and also produce less neurological side effects. Some of the compounds also have some positive inotropic activity and therefore are particularly beneficial in patients with impaired cardiac pump function.

SUMMARY OF THE INVENTION

Thus the invention provides antiarrhythmic agents of the formula:

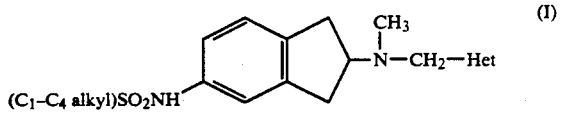

and their pharmaceutically acceptable salts, wherein "Het" is a group of the formula:

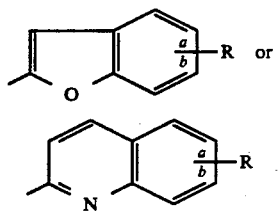

in which R, which is attached to position "a" or "b" of the benzene ring, is a group of the formula —NHSO$_2$(-C$_1$–C$_4$ alkyl).

The invention also provides synthetic intermediates of the formula:

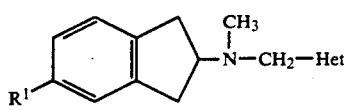

wherein "Het" is a group of the formula:

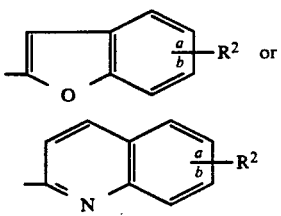

in which
R$^2$ is attached to position "a" or "b" of the benzene ring: and
R$^1$ and R$^2$, which are the same, are both —NO$_2$ or —NH$_2$.

The invention yet further includes the intermediates of the formula:

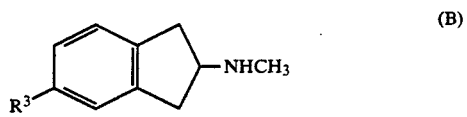

and their acid addition salts (particularly their hydrochloride salts), wherein R$^3$ is —NO$_2$ or —NHSO$_2$(-C$_1$–C$_4$ alkyl).

R and R$^2$ are preferably attached to position "a" of the benzene ring portion of "Het". The preferred alkyl group is methyl. C$_3$ and C$_4$ alkyl groups can be straight or branched chain.

The preferred antiarrhythmic agent of the formula (I) has the structure:

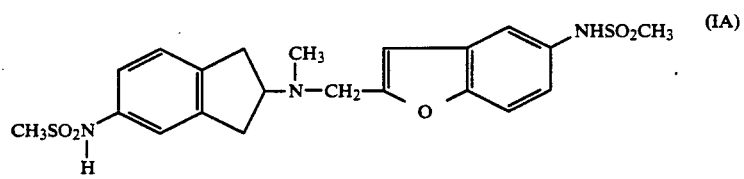

The compounds of the formula (I) are optically active and thus the invention includes the R, S and R/S forms.

The pharmaceutically acceptable salts of the compound of the formula (I) include acid addition salts formed from acids which form non-toxic acid addition salts containing pharmaceutically acceptable anions, such as hydrochloride, hydrobromide, hydroiodide, sulphate or bisulphate, phosphate or hydrogen phosphate, acetate, maleate, fumarate, lactate, tartrate, citrate, gluconate, benzoate, methanesulphonate, besylate and p-toluenesulphonate salts. Also included are the alkali metal salts, especially the sodium and potassium salts. The salts are preperable by conventional techniques.

For assessment of effects of the compounds on atrial refractoriness, guinea pig right hemiatria are mounted in a bath containing physiological salt solution, and one end is connected to a force transducer. Tissues are stimulated at 1 Hz using field electrodes. Effective refractory period (ERP) is measured by introducing premature stimuli ($S_2$) after every 8th basic stimulus ($S_1$). The $S_1S_2$ coupling interval is gradually increased until $S_2$ reproducibly elicits a propagated response. This is defined as the ERP. The concentration of compound required to increase ERP by 25% ($ED_{25}$) is then determined. ERP is also measured in guinea pig right papillary muscles incubated in physiological salt solution. Muscles are stimulated at one end using bipolar electrodes and the propagated electrogram is recorded at the opposite end via a unipolar surface electrode. ERP is determined as above using the extrastimulus technique. Conduction time is obtained from a digital storage oscilloscope by measuring the interval between the stimulus artefact and the peak of the electrogram (i.e. the time required for the impulse to travel along the length of the muscle).

Atrial and ventricular ERP's are also measured in anaesthetised or conscious dogs by the extrastimulus technique whilst the atrium or right ventricle is being paced at a constant rate.

The compounds of the formula (I) can be administered alone but will generally be administered in admixture with a pharmaceutical carrier selected with regard to the intended route of administration and standard pharmaceutical practice. They can be administered both to patients suffering from arrhythmias and also prophylactically to those likely to develop arrhythmias. For example they may be administered orally in the form of tablets containing such excipients as starch of lactose, or in capsules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other solutes, for example, enough salts or glucose to make the solution isotonic.

For administration to man in the curative or prophylactic treatment of cardiac conditions such as ventricular and supraventricular arrhythmias, including atrial and ventricular fibrillation, it is expected that oral dosages of the compounds of the formula (I) will be in the range from 2 to 150 mg daily, taken in and up to 4 divided doses per day, for an average adult patient (70 kg). Dosages for intravenous administration would be expected to be within the range 1.0 to 20 mg per single dose as required. A severe cardiac arrythmia is preferably treated by the i.v. route in order to effect a rapid conversion to the normal rhythm. Thus for a typical adult patient individual tablets or capsules might contain 2 to 50 mg of active compound, in a suitable pharmaceutically acceptable vehicle or carrier. Variations may occur depending on the weight and condition of the subject being treated as will be known to medical practitioners.

Thus the present invention provides a pharmaceutical composition comprising a compound of the formula (I) as defined above or pharmaceutically acceptable salt thereof, together with a pharmaceutically acceptable diluent or carrier.

The invention also provides a method of preventing or reducing cardiac arrhythmias in a human being, which comprises administering to said human an effective amount of a compound of the formula (I) or pharmaceutically acceptable salt thereof, or of a pharmaceutical composition as defined above.

The invention yet further provides a compound of the formula (I) or a pharmaceutically acceptable salt thereof, for use as a medicament, particularly for use as an antiarrhythmic agent.

The invention also provides the use of a compound of the formula (I), or of a pharmaceutically acceptable salt thereof, for the manufacture of a medicament for the prevention or reduction of cardiac arrhythmias.

DETAILED DESCRIPTION OF THE INVENTION

The compounds of the formula (I) can be prepared by the following general routes:

(1) The first route involves the acylation of a compound of the formula (A) in which $R^1$ and $R^2$ are both $-NH_2$, using a $C_1-C_4$ alkanesulphonyl chloride or bromide, or a $C_1-C_4$ alkanesulphonic anhydride. Clearly at least two equivalents of the acylating agent will be required and, of course, the alkanesulphonamido groups in the final product will be the same.

This reaction is typically carried out at room temperature, and optionally in the presence of an acid acceptor such as pyridine, triethylamine, potassium carbonate or sodium bicarbonate. The presence of an acid acceptor is particularly useful when an alkanesulphonyl chloride or bromide is used. It is in fact particularly convenient to carry out the reaction using an alkanesulphonyl chloride in pyridine, the pyridine functioning both as the acid acceptor and as the solvent. The product of the formula (I) can then be isolated and purified by conventional means.

The starting materials of the formula (A) in which $R^1$ and $R^2$ are both $-NH_2$ can be prepared by the reduction of the corresponding compounds in which $R^1$ and $R^2$ are both $-NO_2$ using conventional techniques, e.g. by using $H_2/pd/C$ in ethanol.

The di-nitro starting materials are available as follows:

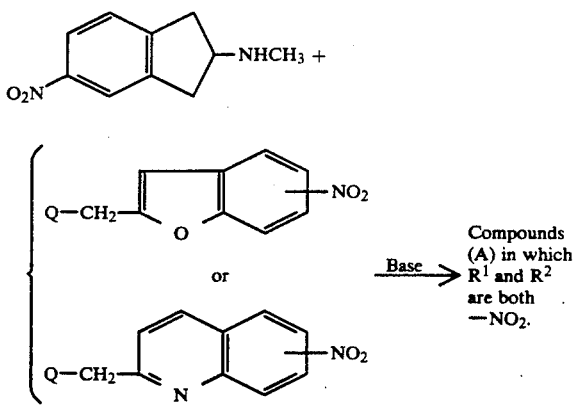

Q is a leaving group such as Cl, Br, I, methanesulphonyloxy, benzenesulphonyloxy or toluenesulphonyloxy. Q is preferably Cl, Br or I, and the reaction is typically carried out in an organic solvent such as ethanol at about room temperature and in the presence of a base such as potassium carbonate or sodium bicarbonate. If necessary, the reaction mixture can be heated at up to the reflux temperature to accelerate the rate of reaction.

The synthesis of 2-methylamino-5-nitroindane is described in detail in Preparations 1 to 3. The nitro-substituted heterocyclic starting materials are either known compounds or can be prepared by methods analogous to the prior art, e.g. as described in certain of the following Preparations.

The compounds of the formula (I) can be prepared as illustrated in the following Examples, in which all temperatures are in °C.:

EXAMPLE 1

5-Methanesulphonamido-2-[N-(5-methanesulphonamidobenzofur-2-ylmethyl)-N-methylamino]indane maleate

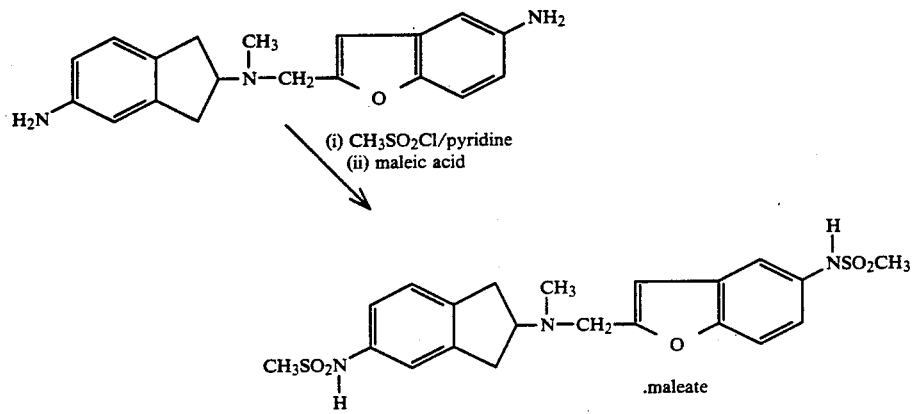

(2) The second route to the compounds of the formula (I) can be illustrated as follows:

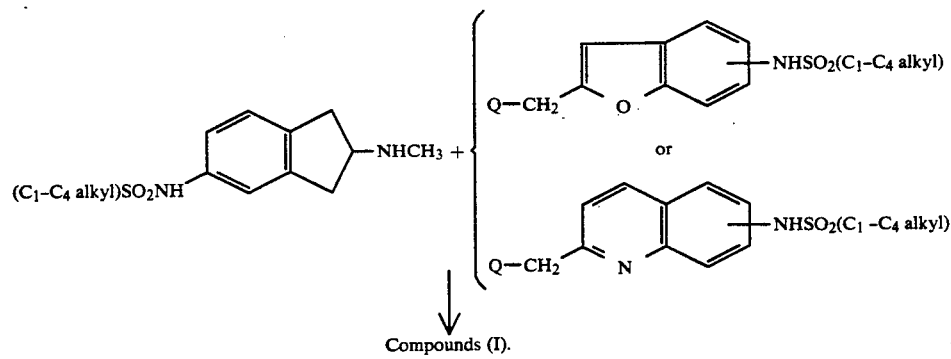

Q is a leaving group such as those defined above, and is preferably Cl or Br. The reaction is typically carried out in the presence of a base, e.g. sodium bicarbonate or potassium carbonate, and in an organic solvent, e.g. acetonitrile, at a temperature of from, say, 20° to 100° C., and preferably under reflux.

The typical preparation of an alkanesulphonamido-substituted indane starting material is described in detail in Preparations 6 to 11. The alkanesulphonamido-substituted heterocyclic starting materials are also available via conventional methods such as those illustrated in the following Preparations.

Clearly this route can be used, if so desired, to prepare compounds of the formula (I) in which the alkanesulphonamido groups are different.

Methanesulphonyl chloride (0.25 ml) was added to a solution of 5-amino-2-[N-(5-aminobenzofur-2-ylmethyl)-N-methylamino]indane (0.3 g) in pyridine (20 ml) and the mixture was stirred for 17 hours at room temperature. The solvent was then removed by evaporation in vacuo to give a gum which was purified by column chromatography on silica eluting with methylene chloride containing methanol (0% up to 1%). The product-containing fractions were combined and evaporated in vacuo to an oil which was taken up in ether, diluted with ethereal maleic acid and the precipitate collected by filtration and dried to give the title compound, yield 0.1 g, m.p. 195° (dec.).

$^1$H-N.m.r. (CDCl$_3$): δ=9.1 (s, 2H); 7.2 (s, 1H); 7.1 (q, 2H); 6.9 (s, 1H); 6.85 (q, 2H); 6.7 (s, 1H); 6.0 (s, 2H); 4.15 (s, 2H); 3.7 (t, 1H); 3.05 (t, 4H); 2.6 (d, 6H); 2.5 (s, 3H).

EXAMPLE 2

5-Methanesulphonamido-2-[N-(6-methanesulphonamidoquinol-2-ylmethyl)-N-methylamino]indane

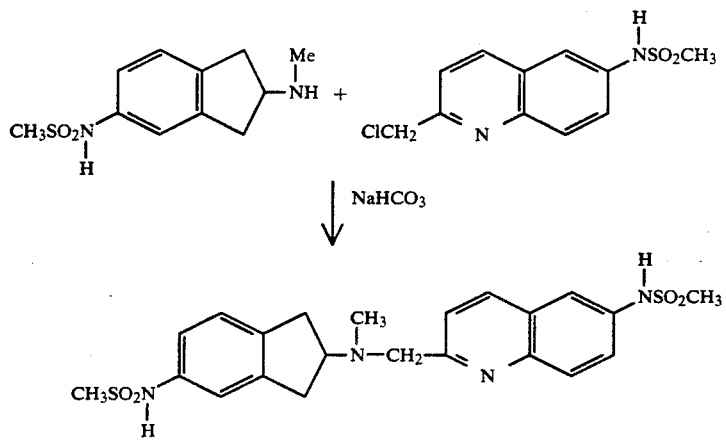

5-Methanesulphonamido-2-methylaminoindane (0.09 g), 2-chloromethyl-6-methanesulphonamidoquinoline (0.1 g) and sodium bicarbonate (0.2 g) were heated under reflux in acetonitrile (10 ml) for 1½ hours. The solvent was then removed by evaporation in vacuo and the residue was taken up in methylene chloride, washed with aqueous sodium bicarbonate, dried (MgSO$_4$) and evaporated in vacuo. The residue was purified by column chromatography on silica eluting with methylene chloride containing methanol (0% up to 2%) and the product-containing fractions were combined and evaporated to give the title compound as a foam, yield 0.09 g. A sample was crystallised from deuterochloroform, m.p. 189°-191°.

Analysis %: Found: C,55.35; H,5.7; N,11.3; Calculated for C$_{22}$H$_{26}$N$_4$O$_4$S$_2$; C,55.7; H,5.5; N,11.8.

$^1$H-N.m.r. (CDCl$_3$): δ=8.1 (q, 2H); 7.75 (s, 1H); 7.70 (s, 1H); 7.5 (q, 1H); 7.2 (d, 1H); 7.15 (s, 1H); 7.0 (d, 1H); 6.4 (s, 1H); 3.9 (s, 2H); 3.6 (quintet, 1H); 3.1 (s, 3H); 3.05 (m, 4H); 3.0 (s, 3H); 2.3 (s, 3H).

The following Preparations, in which all temperatures are in °C., illustrate the preparation of the novel starting materials used in the Examples:

PREPARATION 1

2-Formylaminoindane

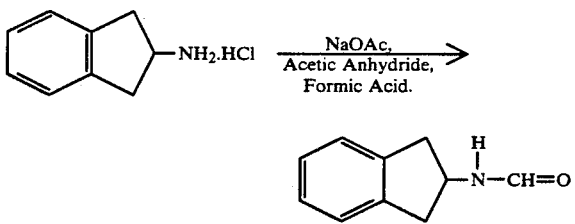

Acetic anhydride (40 ml) and formic acid (20 ml) were mixed and heated at 50° for 15 minutes with stirring. 2-Aminoindane hydrochloride (25 g) (see J. Med. Chem., 1980, 23, page 745) and sodium acetate (20 g) were added to this mixture which was then stirred at room temperature for 24 hours. The reaction mixture was poured into ice/water and extracted three times with methylene chloride. The combined organic layers were washed with water and aqueous sodium carbonate, dried (MgSO$_4$) and evaporated in vacuo to give the title compound, yield 17.6 g, m.p. 72°-74°.

Analysis %: Found: C,74.25; H,7.0; N,8.6; Calculated for C$_{10}$H$_{11}$NO: C,74.5; H,6.9; N,8.7.

$^1$H-N.m.r. (CDCl$_3$): δ=8.0 (s, 1H); 7.1 (s, 4H); 4.7 (m, 1H); 3.4 (dd, 2H); 2.8 (dd, 2H).

PREPARATION 2

2-Formylamino-5-nitroindane

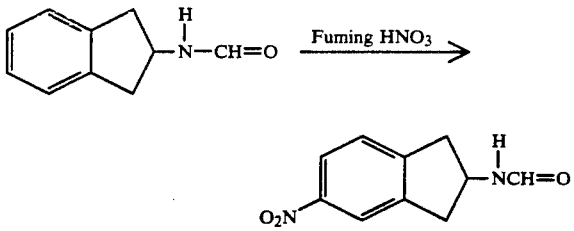

2-Formylaminoindane (15 g) was added portionwise to fuming nitric acid (30 ml, density=1.5 g/ml) whilst keeping the temperature at between 0° and −5°. Stirring was continued for 1 hour at 0° before pouring the reaction mixture onto ice/water and extracting with methylene chloride. The organic layer was washed with aqueous sodium bicarbonate, dried (MgSO$_4$) and evaporated in vacuo to give an oil which was purified by column chromatography on silica eluting with methylene chloride containing hexane (20% down to 0%) and then methylene chloride containing methanol (0% up to 2%). The product-containing fractions were combined and evaporated to give the title compound, yield 7.7 g, m.p. 91°-92°.

Analysis %: Found: C,58.1; H,4.8; N,13.5; Calculated for C$_{10}$H$_{10}$N$_2$O$_3$; C,58.25; H,4.9; N,13.6.

PREPARATION 3

2-Methylamino-5-nitroindane hydrochloride

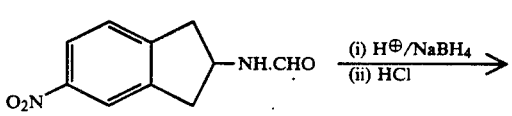

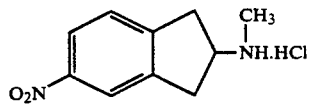

Acetic acid (6.4 ml) was dropwise to a stirred mixture of 2-formylamino-5-nitroindane (4.6 g) and sodium borohydride (4.22 g) in tetrahydrofuran (65 ml) cooled to 0°-5°. Stirring was continued at 0°-5° for 15 minutes before heating the reaction mixture at reflux for 2 hours. The reaction mixture was then evaporated to dryness in vacuo and the residue was diluted with 2M hydrochloric acid, then made basic (to a pH of about 12) with aqueous sodium carbonate and extracted with methylene chloride. The organic layer was dried (MgSO$_4$), evaporated in vacuo and the residue stirred with ethereal hydrogen chloride to afford a precipitate which was filtered and dried to give the title compound, yield 1.5 g, m.p. 221°-223°.

Analysis %: Found: C,52.75; H,5.6; N,12.15; Calculated for C$_{10}$H$_{12}$N$_2$O$_2$.HCl: C,52.5; H,5.7; N,12.25.

PREPARATION 4

2-[N-Methyl-N-(5-nitrobenzofur-2-ylmethyl)amino]-5-nitroindane

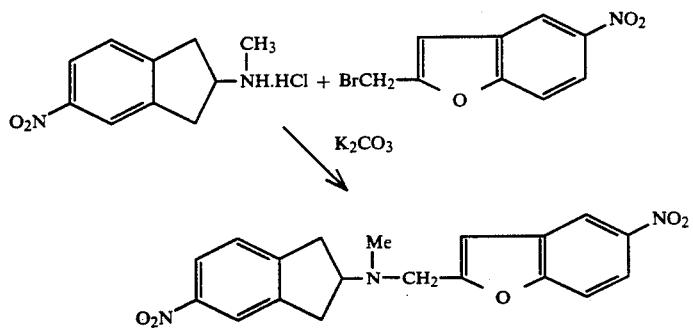

2-Methylamino-5-nitroindane hydrochloride (0.28 g), 2-bromomethyl-5-nitrobenzofuran (0.31 g) and potassium carbonate (0.5 g) were stirred at room temperature in ethanol for 18 hours. A further portion of 2-bromomethyl-5-nitrobenzofuran (0.05 g) was then added and stirring was continued at room temperature for 5 hours. The solvent was evaporated in vacuo and the residue was dissolved in methylene chloride, washed with water, dried (MgSO$_4$) and evaporated to give an oil which was purified by column chromatography on silica eluting with methylene chloride containing methanol (0% up to 1%). The product-containing fractions were combined and evaporated to give a gum which was triturated with diisopropyl ether and the precipitate was filtered off to give the title compound, yield 0.35 g, m.p. 109°-111°.

Analysis %: Found: C,61.9; H,4.6; N,11.3; Calculated for C$_{19}$H$_{17}$N$_3$O$_5$: C,62.1; H,4.7; N,11.4.

$^1$H-N.m.r. (CDCl$_3$): δ=8.3 (d, 1H); 8.0 (m, 3H); 7.5 (d, 1H); 7.3 (d, 1H); 6.7 (s, 1H); 3.9 (s, 2H); 3.5 (m, 1H); 3.2 (m, 4H); 2.4 (s, 3H).

PREPARATION 5

5-Amino-2-[N-(5-aminobenzofur-2-ylmethyl)-N-methylamino]indane

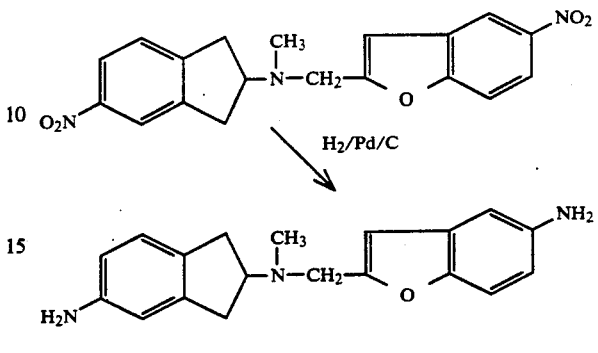

A solution of 2-[N-methyl-N-(5-nitrobenzofur-2-ylmethyl)amino]-5-nitroindane (0.33 g) in ethanol (25 ml) containing 5% Pd/C (0.03 g) was stirred under a hydrogen atmosphere [206.8 kPa (30 p.s.i.)] for 3 hours at room temperature. The catalyst was then removed by filtration and the filtrate evaporated in vacuo to afford the title compound as a gum, yield 0.3 g, which was used directly without further purification.

PREPARATION 6

2-(N-Benzyl-N-methylamino)indane hydrochloride

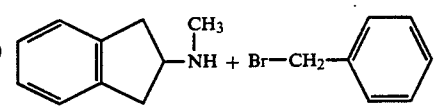

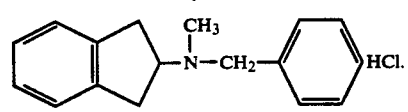

2-Methylaminoindane (0.65 g) (see J. Med. Chem., 1980, 23, page 745), benzyl bromide (0.6 g) and potassium carbonate (1.0 g) were heated under reflux in acetonitrile for 8 hours. The reaction mixture was then filtered and evaporated to dryness in vacuo. The resulting oil was dissolved in ethyl acetate, diluted with ethereal hydrogen chloride and the precipitate collected by filtration and recrystallised from isopropanol to give the title compound, yield 0.5 g, m.p. 204°–206°.

PREPARATION 7 (Alternative to Preparation 6)

2-(N-Benzyl-N-methylamino)indane hydrochloride

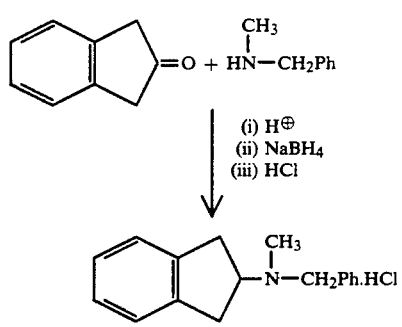

A solution of 2-indanone (5.28 g), N-benzylmethylamine (4.84 g) and 4-toluenesulphonic acid (0.15 g) in toluene (120 ml) was heated under reflux in a Dean and Stark apparatus for 1½ hours by which time all the water produced (approximately 0.8 ml) had been collected by azeotroping. The solvent was then evaporated in vacuo and the residue dissolved in ethanol (150 ml) to which was added sodium borohydride (1.6 g) and the mixture was stirred at room temperature for 17 hours. The solvent was then evaporated in vacuo and the residue carefully diluted with 2M hydrochloric acid (50 ml). The acid solution was extracted twice with methylene chloride (2×100 ml) and the combined organic extracts were evaporated in vacuo to give a residue which was triturated with isopropanol and the resulting precipitate filtered off and dried to afford the title compound, yield 2.5 g, m.p. 204°–206°.

Analysis %: Found: C,74.1; H,7.4; N,5.0; Calculated for $C_{17}H_{19}N.HCl$: C,74.6; H,7.4; N,5.1.

'H-N.m.r. (CDCl$_3$): δ=7.7 (dd, 2H); 7.5 (m, 3H); 7.15 (q, 4H); 4.4 (q, 1H); 4.15 (q, 1H); 4.05 (quintet, 1H); 3.8 (q, 1H); 3.6 (q, 1H); 3.5 (q, 1H); 3.25 (q, 1H); 2.6 (d, 3H).

PREPARATION 8

2-[N-Methyl-N-(4-nitrobenzyl)amino]-5-nitroindane

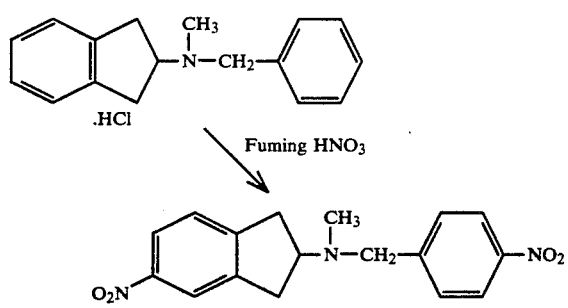

2-[N-Benzyl-N-methylamino]indane hydrochloride (2.6 g) was added portionwise over 10 minutes to fuming nitric acid (25 ml) cooled to −5°. Stirring was continued for a further 2 minutes before the reaction mixture was poured into ice/water. The water was decanted off to leave a gum which was taken up in methylene chloride, washed with water and saturated aqueous sodium bicarbonate, dried (MgSO$_4$) and evaporated in vacuo to give the title compound, yield 2.4 g. A sample (0.1 g) was dissolved in ether and treated with ethereal hydrogen chloride. The resulting precipitate was collected by filtration and dried to give the hydrochloride salt of the title compound, m.p. 210°–212°.

Analysis %: Found: C,55.2; H,5.0; N,11.2; Calculated for $C_{17}H_{17}N_3O_4.HCl.\tfrac{1}{2}H_2O$: C,54.8; H,5.1; N,11.3.

'H-N.m.r. (TFAd): δ=8.8 (s, 1H); 8.7 (t, 1H); 8.35 (d, 2H); 8.1 (d, 1H); 7.9 (m, 1H); 7.6 (d, 1H); 5.0 (d, 1H); 4.7 (m, 1H); 4.6 (d, 1H); 3.8 (m, 4H); 3.0 (s, 3H).

PREPARATION 9

5-Amino-2-[N-(4-aminobenzyl)-N-methylamino]indane

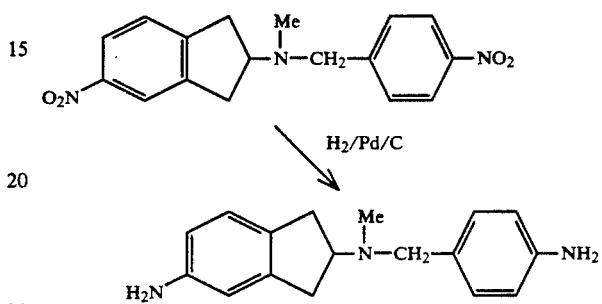

2-[N-Methyl-N-(4-nitrobenzyl)amino]-5-nitroindane (2.3 g) in ethyl acetate (60 ml) containing 5% Pd/C ( . . . g) was stirred under a hydrogen atmosphere [206.8 kPa (30 psi)] for 1 hour at room temperature. The catalyst was then removed by filtration and the filtrate was evaporated to dryness in vacuo. The residue was purified by column chromatography on silica eluting with methylene chloride containing methanol (0% up to 1%). The product-containing fractions were combined and evaporated to give the title compound (1.1 g) as an oil which was used directly without further purification.

PREPARATION 10

5-Methanesulphonamido-2-[N-(4-methanesulphonamidobenzyl)-N-methylamino]indane

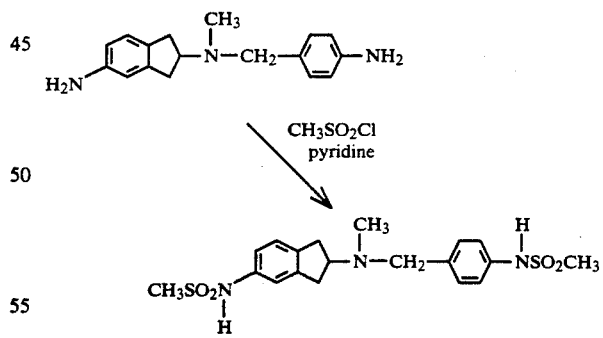

Methanesulphonyl chloride (0.53 ml) was added to 5-amino-2-[N-(4-aminobenzyl)-N-methylamino]indane (1.1 g) in pyridine and the reaction mixture was stirred at room temperature for 17 hours. The solvent was then removed by evaporation in vacuo and the residue taken up in methylene chloride, washed with aqueous sodium bicarbonate, dried (MgSO$_4$) and evaporated in vacuo. The resulting gum was purified by column chromatography on silica eluting with methylene chloride containing methanol (0% up to 2%). The product-containing fractions were combined and evaporated to dryness in vacuo to give a colourless foam. This foam was dissolved in chloroform and the solution was evaporated to dryness in vacuo to give the title compound as a colourless foam, yield 0.2 g.

Analysis %: Found: C,54.0; H,6.0; N,9.5; Calculated for $C_{19}H_{25}N_3O_4.2/3$ $CHCl_3$*: C,53.9; H,5.9; N,9.6.

* The fact that the product was a solvate was detected and quantified by 'H-n.m.r.

'H-N.m.r. (TFAd): δ=7.72 (s, 1H); 7.63 (t, 1H); 7.45 (d, 2H); 7.4 (t, 2H); 7.3 (s, 1H); 4.8 (d, 1H); 4.5 (m, 1H); 4.35 (d, 1H); 3.6 (m, 4H); 3.2 (d, 6H): 2.9 (d, 3H).

PREPARATION 11

5-Methanesulphonamido-2-methylaminoindane

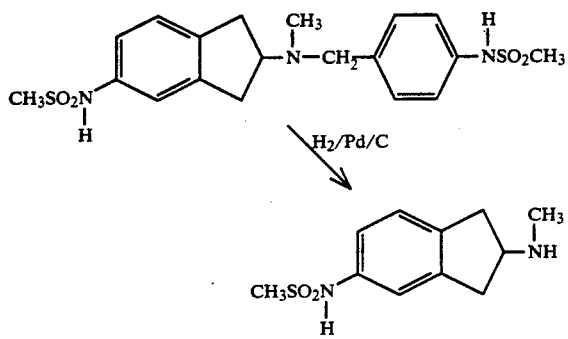

2-[N-(4-Methanesulphonamidobenzyl)-N-methylamino]-5-methanesulphonamidoindane (0.175 g) in ethanol (20 ml) containing 5% Pd/C (0.02 g) was stirred under a hydrogen atmosphere [275.8 kPa (40 p.s.i.)] for 3½ hours at 40°. The catalyst was then removed by filtration and the filtrate evaporated to dryness in vacuo to give the title compound as an oil, yield 0.09 g, which was used directly without further purification.

PREPARATION 12

(A) 4-(Isopropylideneaminoxy)nitrobenzene

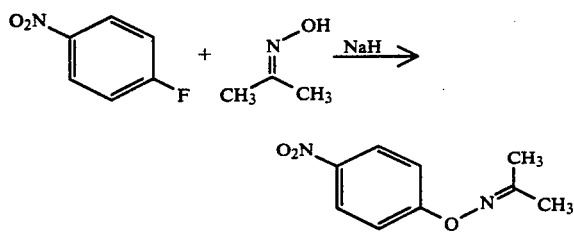

A solution of propanone oxime (30 g, 0.4 mole) in dry tetrahydrofuran (300 ml) was added slowly to a suspension of sodium hydride (10.8 g, 0.45 mole) in dry tetrahydrofuran (50 ml). After gas evolution was complete, dimethylsulphoxide (100 ml) and 4-fluoronitrobenzene (57.85 g, 0.41 mole) were added and the reaction mixture was stirred at room temperature for 2 hours. The reaction mixture was then poured into water and extracted three times with ether. The combined ether extracts were washed with water, dried (MgSO$_4$) and evaporated to give the title compound which was granulated in hexane and filtered, yield 67 g. A sample (7 g) was recrystallised from ethanol, yield 5 g, m.p. 104°-106°.

Analysis %: Found: C,55.6; H,5.05; N,14.35; Calculated for $C_9H_{10}N_2O_3$: C,55.7; H,5.2; N,14.4.

(B) 2-Methyl-5-nitrobenzofuran

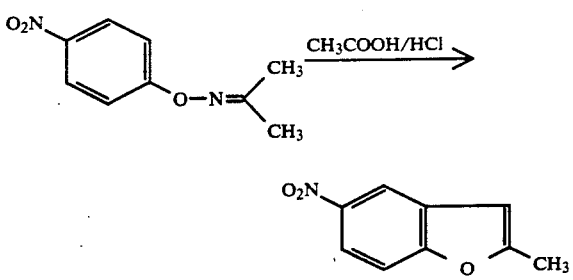

4-(Isopropylideneaminoxy)nitrobenzene (60 g, 0.309 mole) was added to glacial acetic acid (530 ml) containing gaseous hydrogen chloride (25 g) and the mixture was heated at 100° for 18 hours. The solvent was evaporated and the residue azeotroped with cyclohexane to give an oil which was diluted with water and extracted three times with methylene chloride. The combined organic extracts were washed with 10% aqueous sodium hydroxide solution and water, dried (MgSO$_4$) and evaporated to give the title compound, yield 46 g. A sample (5 g) was recrystallised from isopropanol, yield 2.5 g, m.p. 93°-95°.

Analysis %: Found: C,61.2; H,4.1; N,7.9; Calculated for $C_9H_7NO_3$: C,61.0; H,4.0; N,7.9.

(C) 2-Bromomethyl-5-nitrobenzofuran

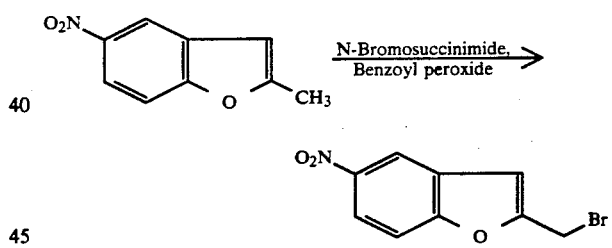

N-Bromosuccinimide (1.1 g, 6.2 mmole) was added portionwise to a solution of 2-methyl-5-nitrobenzofuran (1.0 g, 5.6 mmole) and benzoyl peroxide (50 mg) in carbon tetrachloride (50 ml) and the reaction mixture was heated at reflux temperature for 6 hours in the presence of bright light. The reaction mixture was then cooled, filtered and the filtrate evaporated to dryness. The residue was recrystallised from petroleum ether to give the title compound, yield 0.75 g, m.p. 96°-98°.

Analysis %: Found: C,41.7; H,2.4; N,5.3; Calculated for $C_9H_6BrNO_3$: C,42.2; H,2.4; N,5.5.

PREPARATION 13

(A) 6-Amino-2-methylquinoline

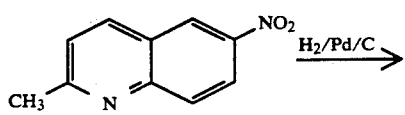

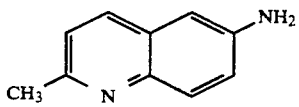

2-Methyl-6-nitroquinoline (18.8 g) was stirred under a hydrogen atmosphere at 206.8 kPa (30 p.s.i.) for 2 hours in ethanol solution containing 5% Pd/C. The catalyst was then removed by filtration, the filtrate evaporated to small volume in vacuo, and the resultant precipitate collected by filtration, washed with ethanol and ether, and dried to give the title compound, yield 13.2 g, m.p. 188°–189°.

Analysis %: Found: C,75.7; H,6.4; N,17.6; Calculated for $C_{10}H_{10}N_2$: C,75.9; H,6.4; N,17.7.

(B) 6-Methanesulphonamido-2-methylquinoline

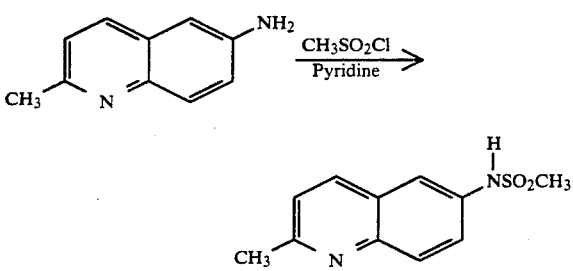

Methanesulphonyl chloride (6.2 ml) was added dropwise to a stirred solution of 6-amino-2-methylquinoline (12.5 g) in pyridine (100 ml) cooled to 5°. Stirring was continued for 17 hours at room temperature. The pyridine was then removed by evaporation in vacuo, the residue diluted with aqueous sodium bicarbonate, and extracted three times with methylene chloride. The combined organic extracts were combined, dried (MgSO₄) and evaporated in vacuo to give the title compound, yield 13.0 g, m.p. 151°–153°.

Analysis: Found: C,55.4; H,5.2; N,11.6; Calculated for $C_{11}H_{12}N_2O_2S$: C,55.9; H,5.1; N,11.9.

(C)
6-Methanesulphonamido-2-methylquinoline-1-oxide

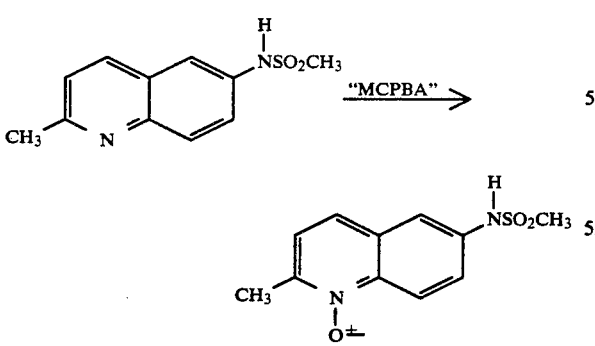

m-Chloroperbenzoic acid ("MCPBA") (5.2 g) was added portionwise to a solution of 6-methanesulphonamido-2-methylquinoline (6 g) in methylene chloride and stirring was continued for 17 hours. The reaction mixture was then diluted with aqueous sodium bicarbonate and the organic layer was separated. The aqueous layer was extracted with methylene chloride. The combined organic layers were washed with aqueous sodium bicarbonate, dried (MgSO₄) and evaporated in vacuo to give a solid which was recrystallised from ethanol to give the title compound, yield 1.6 g, m.p. 241°–243°.

Analysis %: Found: C,52.5; H,4.95; N,11.0; Calculated for $C_{11}H_{12}N_2O_3S$: C,52.4; H,4.8; N,11.1

(D) 2-Chloromethyl-6-methanesulphonamidoquinoline

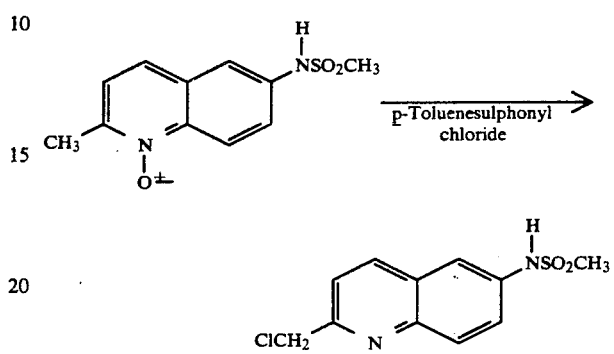

6-Methanesulphonamido-2-methylquinoline-1-oxide (1.65 g) and p-toluenesulphonyl chloride (1.72 g) were heated under reflux for 1 hour in 1,2-dichloroethane solution, and the reaction mixture was then stood at room temperature for 17 hours. The reaction mixture was then washed twice with aqueous sodium bicarbonate, dried (MgSO₄) and evaporated in vacuo. The residue was purified by column chromatography on silica eluting with methylene chloride containing methanol (0% up to 1%). The product-containing fractions were combined and evaporated to give a gum which solidified when triturated with ether. Recrystallisation from toluene gave the title compound, yield 0.75 g, m.p. 160°–162°.

Analysis %: Found: C, 49.3; H, 3.9; N, 10.1; Calculated for $C_{11}H_{11}N_2O_2ClS$: C,48.8; H,4.1; N,10.35.

PREPARATION 14

(A) 2-Bromomethyl-6-nitrobenzofuran

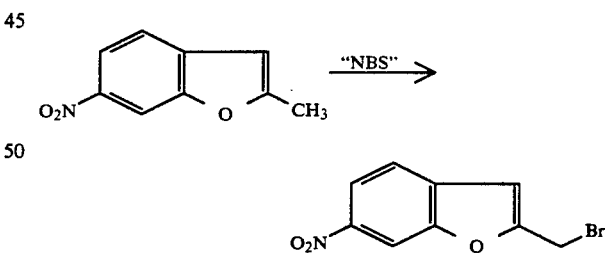

N-Bromosuccinimide ("NBS") (1.11 g, 6.2 mmole) was added to a solution of 2-methyl-6-nitrobenzofuran (1.00 g, 5.65 mmole) and azobisisobutyronitrile (20 mg) in carbon tetrachloride and the mixture was heated at reflux temperature for 1½ hours in the presence of a bright light. The solvent was then evaporated and the residue dissolved in methylene chloride, washed with water, dried (MgSO₄), evaporated to dryness and purified by column chromatography on silica eluting with methylene chloride/hexane (7:3). The product-containing fractions were combined and evaporated to give the title compound, yield 1.43 g. ¹H-N.m.r. clearly showed that the product contained 20% of 2-dibromomethyl-6- nitrobenzofuran, however, it was not considered necessary to remove this.

We claim:

1. A disulfonamide compound of the formula:

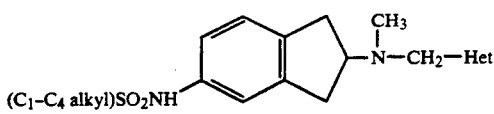

or a pharmaceutically acceptable salt thereof, wherein "Het" is benzo-fused heterocyclic group of the formula:

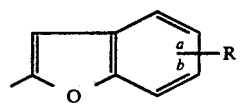

wherein R is $-NHSO_2(C_1-C_4\ alkyl)$ attached to either the a- or b- position of the benzene ring of said group.

2. A compound as claimed in claim 1 wherein R is attached to the a- position of the benzene ring of said group.

3. A compound as claimed in claim 2 wherein R and the $(C_1-C_4\ alkyl)SO_2NH-$ group attached to the 5-position of the indane ring are both $-NHSO_2CH_3$.

4. A compound as claimed in claim 3 wherein "Het" is 5-methanesulphonamidobenzofur-2-yl.

5. 5-Methanesulphonamido-2-[N-(5-methanesulphonamidobenzofur-2-ylmethyl)-N-methylamino]indane.

6. A pharmaceutical composition comprising a pharmaceutically acceptable carrier or diluent and an effective anti-arrhythmic amount of a compound as claimed in claim 1.

7. A method for preventing or reducing cardiac arrhythmias in the treatment of a subject afflicted with an impaired cardiac pump function, which comprises administering to said subject an effective anti-arrhythmic amount of a compound as claimed in claim 1.

8. A tertiary organic amine compound of the formula:

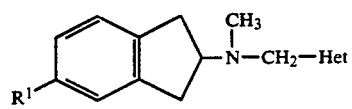

wherein
$R^1$ is nitro or amino; and
"Het" is a benzo-fused heterocyclic group of the formula:

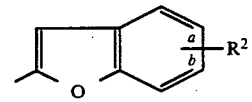

wherein $R^2$ is nitro or amino attached to either the a- or b- position of the benzene ring of said group; with the proviso that $R^1$ and $R^2$ are always both the same.

* * * * *